United States Patent [19]

Yee et al.

[11] Patent Number: 5,211,184
[45] Date of Patent: May 18, 1993

[54] METHOD AND APPARATUS FOR ACUPUNCTURE TREATMENT

[76] Inventors: Hsiao P. Yee; Hsiao C. Yee, both of 7338 23 Ave. NE., Seattle, Wash. 98115

[21] Appl. No.: 694,552

[22] Filed: May 2, 1991

[51] Int. Cl.$^5$ .......................... A61N 1/04; A61N 1/22
[52] U.S. Cl. .................................. 128/802; 128/803; 128/421; 128/907
[58] Field of Search ................. 128/421, 422, 423 W, 128/798, 799, 803, 907, 802, 644; 604/20

[56] References Cited

U.S. PATENT DOCUMENTS

| | | | |
|---|---|---|---|
| 160,753 | 11/1985 | Pomeranz | 128/421 |
| 675,494 | 12/1963 | Gilman | 128/423 W |
| 2,216,800 | 10/1989 | Wu | 128/907 |
| 3,508,541 | 4/1970 | Westbrook | 128/644 |
| 3,900,020 | 5/1974 | Lock | 128/907 |
| 4,926,879 | 5/1990 | Sevrain | 128/421 |

*Primary Examiner*—William E. Kamm
*Assistant Examiner*—Samuel Gilbert
*Attorney, Agent, or Firm*—Robert W. Jenny

[57] ABSTRACT

The apparatus comprises a bandage assembly further comprising a bandage, a contact point and at least two electrode assembly installation components integrated into the bandage; an electrode assembly installed in each installation component, a source for electrical signals, and conductors to carry the signals to the electrode assemblies. The bandage assembly is attached by straps or other appropriate means to a person with the contact point contacting a specific anatomic point and oriented in a specific direction relative to a selected anatomic feature. With the bandage so installed the electrode assemblies in the installation components are positioned precisely at acupuncture points. Treatment occurs when the signals from the source are applied to the electrode assemblies. Each electrode assembly comprises a body and a wick-like electrode inserted through the body. The body is hollow and filled with electrically conductive fluid which, when absorbed by the electrode, renders the electrode conductive. Conductors from the signal source are connected to first ends of the electrodes. Their second ends contact the acupuncture points. The installation fittings and bodies are threaded to provide adjustment of the pressure of the electrodes on the acupuncture points. The pattern of the electrical signals precisely simulates successively the electrical brain waves produced during the four stages of sleep.

3 Claims, 1 Drawing Sheet

FIG. 1
FIG. 2
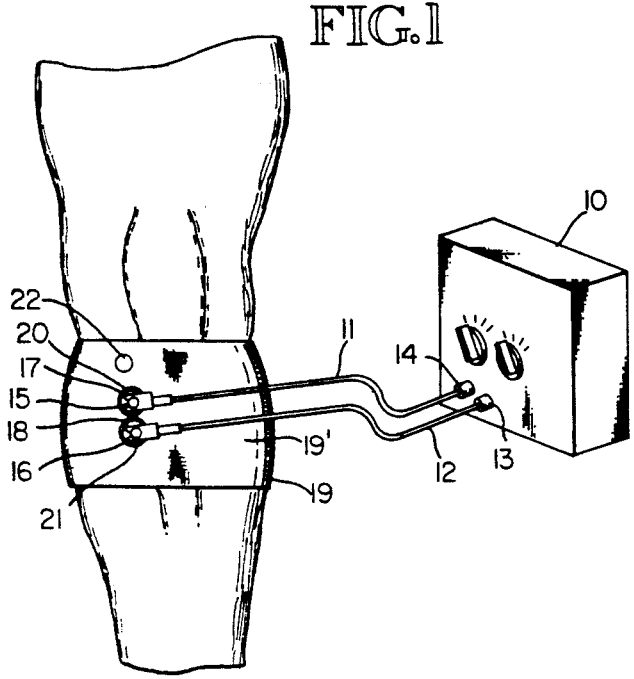
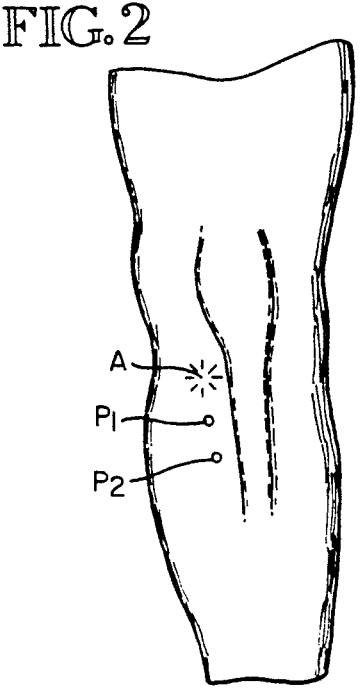
FIG. 1A
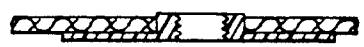
FIG. 3
FIG. 4
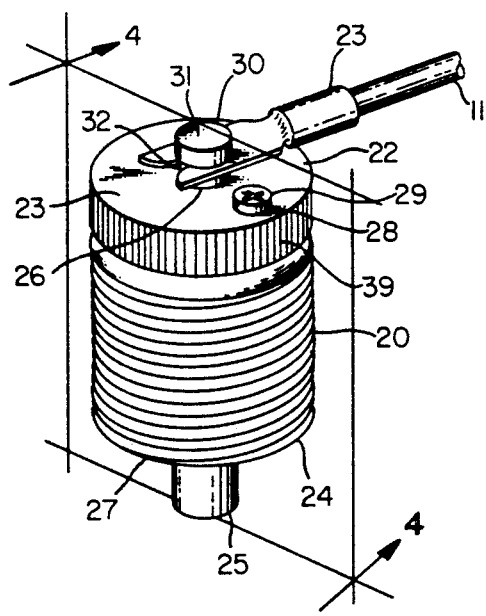
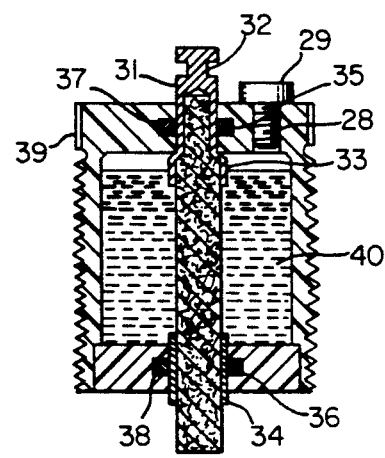

METHOD AND APPARATUS FOR ACUPUNCTURE TREATMENT

BACKGROUND OF THE INVENTION

1. Field:

The subject invention is in the fields of practicing medicine and apparatus used in such practice. More specifically it is in the fields of medical practice termed acupuncture and apparatus used in practicing acupuncture. Acupuncture has been practiced for thousands of years. The practice involved puncturing the patient's skin in specific areas and, if appropriate, manipulating the needles to influence their effect. Recently the needles are electrically energized with variable low voltage signals. Still more recently, the needles are replaced in some instances with electrodes which contact but do not puncture the skin. The term acupuncture has been retained for practice using electrodes even though puncturing does not occur. The subject invention is in the field of practice which incorporates electrodes rather than needles and is directed toward enabling lay people to safely and effectively administer acupuncture treatments.

2. Prior Art:

There is no prior art method and/or apparatus known to the subject inventors for safe and effective administration of acupuncture treatment by lay people. The U.S. Patents listed below cover a sampling of related prior art:

| | |
|---|---|
| 3,900,020 | 4,759,718 |
| 3,908,664 | 4,848,357 |
| 4,180,079 | 4,895,149 |
| 4,267,838 | 4,981,146 |

For patient self-treatment without medical profession involvement it is necessary that electrodes be used instead of needles. Use of electrodes is shown in several of the prior art patents. Also, it is necessary to provide apparatus for accurate, proper positioning of the electrodes. U.S. Pat. No. 4,267,838 teaches the use of electrodes and apparatus for accurate and proper positioning of electrodes in a person's ear. The part which fits into the ear must be molded specifically to fit the ear in which it will be used. This patent does not teach method or apparatus for locating electrodes at any other acupuncture or points except those in the ear.

U.S. Pat. No. 4,759,718 shows articles of clothing intended to teach the locations of acupuncture and pressure points on the human body. The garments are aligned with the wearer's backbone and target marks indicate the general locations of the points. However, this apparatus does not adequately take into account the great varieties of sizes and shapes of human bodies or of the anatomical variations between people of similar sizes and shapes and therefore would not enable reliably effective acupuncture treatment by a lay person.

Accordingly, the primary objective of the subject invention is provision of a method and apparatus which enables a lay person to safely and effectively perform acupuncture treatments at points anywhere on the human body. A second objective is that the apparatus adapt to the varieties and shapes of human bodies with no requirement for especially made parts to fit specific points on specific people. Other objectives will be apparent from the following descriptions.

SUMMARY OF THE INVENTION

The subject invention is a method and apparatus for administering acupuncture treatment. The apparatus comprises two or more electrodes installed in a bandage assembly, so termed for purposes of this disclosure. The bandage assembly also incorporates a reference point contact. In use the bandage assembly is installed with the reference point contact contacting a specific anatomical point such as a specific protuberance caused by a portion of the head of the tibia in the person's leg. The electrodes are installed and positioned with reference to the contact point so that the electrodes contact the body at well known acupuncture points.

In a preferred embodiment the electrode assemblies comprise a wick-like electrode, a reservoir for electrically conductive fluid, an electrical connection on the electrode and a threaded exterior on the reservoir. The electrode assemblies are threaded into internally threaded electrode assembly installation fittings integrated into the bandage assembly. The wick-like contact elements are made conductive by being saturated with the electrically conductive fluid. The bandage assembly is also specifically aligned with respect to anatomical features either by the nature of the bandage or by using markings on the bandage and aligning the markings with the anatomical features. Because of the design of the electrodes the distribution of electrical currents underneath the acupuncture points is similar to that achieved with needles which puncture the skin.

The apparatus also includes an electrical power source for electrically energizing each electrode through electrical conductors connecting the power source to the electrodes in the electrode assemblies, one conductor to each electrode. The electrical power is supplied by batteries and incorporates a microcomputer which controls an electronic apparatus which generates the electrical signals applied to the electrodes. The microcomputer and electronic apparatus are used with but not part of the subject invention and are obtainable from the I.H.E. Corporation, 7030 35th Ave N.E., Seattle, Wash. 98115. The electrical signals simulate successively the electroencephalographic signals of all four stages of sleep. As far as is known this is the first use of electroenaphalographic waves of stages of sleep on medical apparatus.

In use the bandage assembly is fitted in place on a person with the contact point on or surrounding the chosen anatomical point with the bandage assembly aligned relative to a pertinent anatomical feature and with electrode assemblies installed and automatically positioned to contact the desired acupuncture points. The electrode assemblies are then adjusted by turning them to produce comfortable, firm contact between the wick-like electrodes and the person's skin at the acupuncture points. Then conductors from the power supply are connected to the electrodes, one to each electrode, and the power supply is turned on, the signal strengths adjusted and an automatic timer in the power supply set to turn off the power supply after a preset period of time. The techniques for turning on the power, adjusting the signal strengths and setting the timer are obvious from the features of the signal generating equipment, particularly when following appropriate direction by an acupuncturist.

Using the subject apparatus, the acupuncture treatment method comprises the steps of:

1. Providing bandage assemblies in a range of sizes, each bandage assembly having a specific dimension, a contact point for contacting at least one reference point and at least two electrode assemblies integrated into the bandage assembly and precisely positioned with respect to at least one contact point and the specific dimension of the bandage.

2. Providing a controllable electrical signal source having a wave form simulating, in succession, brain waves during stages of sleep. 3. Providing electrical conductors from the signal source, one to each of the two electrode assemblies.

4. Installing at least one bandage assembly on the person with the contact point on the reference point and the specific dimension aligned specifically relative to the anatomical reference point.

5. Controlling the signal source to provide the desired signals to the two electrodes.

The method and apparatus of the invention will be described in more detail below with reference to the attached drawings.

BRIEF DESCRIPTION OF THE DRAWINGS

FIG. 1 is a view of one embodiment of the invention in use on a persons leg.

FIG. 1A is a section of an electrode assembly installation fitting, indicating its integration into the bandage used in the subject embodiment of the invention.

FIG. 2 is a view of a leg illustrating a protuberance used as an anatomical reference point and the related acupuncture points.

FIG. 3 is a perspective view of an electrode assembly.

FIG. 4 is a sectional view of the electrode assembly taken at 4—4 in FIG. 3.

DETAILED DESCRIPTION OF THE INVENTION

The subject invention is a method and apparatus which enables safe, effective acupuncture treatment by lay persons. The apparatus, one embodiment of which is shown in FIG. 1, in the form used at a person's knee, comprises a battery powered signal source 10, conductors 11 and 12 from output terminals 13 and 14 on the source to electrode assemblies 15 and 16 installed in electrode assembly installation fittings 17 and 18. A suitable signal source is available from the I.H.E. Corporation, 7030 35th Ave. N.E., Seattle, Wash. 98115. The fittings are integrated into bandage 19 as parts of a bandage assembly 19¹ and are threaded internally. The bandage in this embodiment of the invention is essentially rectangular, having a long dimension and a width. FIG. 1A is a section of fitting 17 having a thin flange 17' attached by adhesive to bandage 19. The threaded exteriors 20 and 21 of the electrode assemblies are threaded into the fittings variable distances to adjust the pressures of the electrodes of the assemblies on the skin areas they contact.

The bandage assembly is adjusted to fit the leg, held in place by straps not visible in this view and positioned with contact point 22 on an anatomical reference point, in this case one of the protuberances on the skin caused by a portion of the top of the tibia in the leg. The electrode assemblies are located such that with the contact point positioned on the reference point and the long dimension of the bandage at right angles to the long dimension of the tibia, the electrode assemblies are positioned within 5 mm of the centers of the selected acupuncture points. The bandage assemblies in this embodiment can be used either side out, fitting one leg with one side out and the other leg with the other side out.

FIG. 1A is a sectional view illustrating installation fitting 17 integrated into the bandage. The fitting is plastic, has a thin, flexible flange 17'; and is adhesively attached to the bandage.

FIG. 2 is a view of a leg with a reference point indicated by the letter A and two related acupuncture points $P_1$ and $P_2$.

FIG. 3 illustrates an electrode assembly 15 having an exterior surface 20 threaded for adjustment purposes as previously described. Surface 20 is the exterior of body 22 of the assembly. Body 22 in a container having a top 23 and a bottom 24, not visible in this view. Electrode 25 extends through holes 26 and 27 in the top and bottom, hole 26 being visible in this view. It is made from absorbent material such as that used in marking pens. The body is hollow and filled with conductive fluid through opening 28 which is sealed by cap 29, threaded into the threaded opening. The fluid saturates the electrode and renders it electrically conductive. End 30 of the electrode is covered by a metallic cap 31 which is grooved (groove 32) to facilitate retention of clip 23 at the end of conductor 11.

FIG. 4 is a sectional view of the electrode assembly, taken at 4—4 in FIG. 3 with parts and features numbered as in FIG. 3. Note that the electrode is inserted into the body through the bottom and that shoulder 33 limits the amount of insertion. Sleeve 34 on the electrode and cap 31 are engaged by O ring seals 35 and 36 in grooves 37 and 38 to prevent leakage of the fluid 40 from the body. Knurled portion 39 on the body facilitates its adjustment.

The method of using the described apparatus comprises the steps of

1. Providing bandage assemblies in a range of sizes, each bandage assembly having a contact point for contacting a reference point on the human body and at least two electrode assemblies integrated into the bandage assembly and precisely positioned with respect to the contact point and a specific dimension of the bandage.

2. Providing a controllable electrical signal source having a wave form simulating, in succession, brain waves during stages of sleep.

3. Providing at least two electrical conductors from the signal source to the at least two electrode assemblies, one for each electrode assembly.

4. Installing at least one bandage assembly on a person with the contact point on the reference point and the specific dimension aligned specifically relative to one of the person's anatomical features.

5. Controlling the signal source to provide the signals to the at least two electrodes.

The three salient steps are (1) the provision of bandages having the contact points and electrode assemblies with the assemblies positioned with respect to the contact point and a specific dimension of the bandage, (2) installing the bandage assemblies as noted and (3) providing the successive electrical signal patterns. Knobs 13' and 14' are used to turn the signal power on and off and to control signal strength.

The bandages may also be held in place on a person with adhesive or adhesive tapes in locations not adaptable to the use of ties or straps. The bandages may also be marked, with a line for example, for use in properly orienting the bandage. For example, a bandage intended for use on a human backbone has a contact point for placement on the protuberance caused by a particular vertebra, has a line on it for facilitating its proper alignment with respect to the backbone and is held in place by adhesive tape.

It is considered to be understood from this description that the invention meets its objectives. The bandage assembly can be readily and properly installed by persons of ordinary skill in the art; the electrical connections and operation of the power supply are also within the capabilities of such persons. Therefore lay persons can safely and effectively perform acupuncture treatments on themselves at home, significantly reducing the costs of such treatments and making them available to a broader segment of the population. Achievement of the first objective depends on achieving the second: i.e. making the bandage assemblies adaptable to the wide variety of sizes and shapes of the human body. Also the apparatus is not complicated and is readily manufacturable at reasonable cost.

It is also considered to be understood that while certain embodiments of the invention are described herein, other embodiments and modifications of those described are possible within the scope of the invention which is limited only by the attached claims.

We claim:

1. Acupuncture treatment apparatus for use on a human body having anatomical reference points, anatomical reference features and at least two acupuncture points, said treatment apparatus comprising: a bandage assembly, an electrical signal source apparatus, at least two electrical conductors and at least two electrode assemblies each having an electrode, said bandage assembly comprising a bandage, a contact point and at least two electrode assembly installation fittings, said electrode assemblies being mounted in said fittings, said contact point and at least two installation fittings being integrated into said bandage and positioned relative to each other such that when said contact point is in contact with one of said reference points and said bandage is properly aligned with respect to one of said anatomical reference features, said at least two electrode assemblies are positioned at two of said acupuncture points and each of said electrodes contacts one of said acupuncture points, said signal source apparatus being electrically connected to said electrodes of said at least two electrode assemblies by said at least two electrical conductors, each of said at least two electrode assemblies further comprising a hollow body having first and second holes and said electrode being inserted through said body via said first and second holes, said electrode being made of wick-like material, said body being filled with electrically conductive fluid, said electrode being saturated by said electrically conductive fluid and thereby becoming electrically conductive.

2. The acupuncture treatment apparatus of claim 1 in which said at least two electrode assemblies are adjustably mounted in said at least two installation fittings.

3. An acupuncture treatment method for a person having at least one anatomical reference point and at least two acupuncture points, said method comprising the steps of:

providing bandage assemblies in a range of sizes, each bandage assembly having a specific dimension, a contact point for contacting said at least one reference point and at least two electrode assemblies each comprising an electrode integrated into said bandage assembly and precisely positioned with respect to said at least one contact point and said specific dimension of the bandage;

providing a controllable electrical signal source having a wave form simulating, in succession, brain waves during stages of sleep;

providing at least two electrical conductors from said signal source to said at least two electrode assemblies;

installing at least one bandage assembly on said person with said contact point on said reference point and said specific dimension aligned specifically relative to said at least one anatomical reference point so that each electrode contacts one acupuncture point;

connecting said at least two conductors to said signal source and said at least two electrode assemblies, and controlling the signal source to provide said signals to said at least two electrodes.

* * * * *